United States Patent [19]
Kato et al.

[11] Patent Number: 5,597,713
[45] Date of Patent: Jan. 28, 1997

[54] PROCESS FOR PRODUCING CDNAS WITH COMPLETE LENGTH, PROCESS FOR PRODUCING INTERMEDIATES THEREOF AND PROCESS FOR PRODUCING VECTORS CONTAINING CDNAS WITH COMPLETE LENGTHS

[75] Inventors: Seishi Kato; Shingo Sekine, both of Sagamihara, Japan

[73] Assignees: The Kanagawa Academy of Science and Technology Foundation, Kanagawa; Sagami Chemical Research Center, Tokyo, both of Japan

[21] Appl. No.: 244,188

[22] PCT Filed: Sep. 22, 1993

[86] PCT No.: PCT/JP93/01359

§ 371 Date: Jul. 25, 1994

§ 102(e) Date: Jul. 25, 1994

[87] PCT Pub. No.: WO94/08001

PCT Pub. Date: Apr. 14, 1994

[30] Foreign Application Priority Data

Sep. 25, 1992 [JP] Japan .................................. 4-280932
Mar. 3, 1993 [JP] Japan .................................. 5-067589

[51] Int. Cl.$^6$ .......................... C12N 15/11; C12N 15/64; C12P 19/34
[52] U.S. Cl. ................. 435/91.41; 435/91.5; 435/91.51; 435/91.52; 536/23.1; 536/24.33
[58] Field of Search ............................... 435/91.4, 91.41, 435/91.5, 91.51, 91.52; 536/23.1, 24.33

[56] References Cited

PUBLICATIONS

Hogrefe et al. (1990), J. Biol. Chem. 265(10):5561–5566.
Egli et al. (1992), Proc. Natl. Acad. Sci. USA 89:534–538.
Benevides et al. (1986), Biochemistry 25:41–50.
Edery et al. (1995), Mol. Cell. Biol. 15(6): 3363–3371.

*Primary Examiner*—Mindy Fleisher
*Assistant Examiner*—Philip W. Carter

[57] ABSTRACT

A process for providing cDNAs containing full primary structure information of proteins by selectively synthesizing full-length cDNAs containing sequences starting from the capped region of mRNAs is disclosed. The invention provides a process for producing an intermediate for the synthesis of a full-length cDNA, which comprises the steps of treating mRNA extracted from cells to eliminate the phosphate group from the 5' end of an uncapped degraded mRNA; decapping from the 5' end of a capped intact mRNA; and ligating either a DNA oligonucleotide or a DNA-RNA chimeric oligonucleotide represented by the following general formula [I] to the 5' end phosphate group formed in the above step by the action of T4 RNA ligase, thereby selectively adding either the DNA oligonucleotide or the DNA-RNA chimeric oligonucleotide having an arbitrary sequence to the 5' end of the intact mRNA.

$$5'\text{-}dN_1\text{-}dN_2\text{-} \ldots \text{-}dN_m\text{-}N_1\text{-}N_2\text{-} \ldots \text{-}N_n\text{-}3' \quad [I]$$

The present invention also provides a process for synthesizing a full-length cDNA, which comprises linking a double-stranded DNA primer having a dT tail by annealing to a poly(A) tail of the 3' end of the intact mRNA having the DNA oligonucleotide or the DNA-RNA chimeric nucleotide added at the 5' end produced by the above-mentioned process, and then synthesizing the first strand cDNA complementary to the intact mRNA by a reverse transcriptase.

7 Claims, 2 Drawing Sheets

PROCESS FOR PRODUCING CDNAS WITH COMPLETE LENGTH, PROCESS FOR PRODUCING INTERMEDIATES THEREOF AND PROCESS FOR PRODUCING VECTORS CONTAINING CDNAS WITH COMPLETE LENGTHS

TECHNICAL FIELD

The present invention relates to a process for synthesizing a full-length cDNA from mRNA. This invention enables screening of proteins useful in industry and mass production of the proteins.

BACKGROUND ART

Bio-active proteins produced by cells have been widely utilized in industry as materials for medicines, diagnosis, biosensors, bio-reactors and so on. The progress of gene technology has facilitated the discovery of these proteins and enabled us to produce a large amount of the proteins. The fundamental technology is a cDNA cloning technique.

Information on the amino acid sequence of a protein is encoded by mRNA. If the mRNA is converted to a corresponding DNA, i.e., a complementary DNA (cDNA), the cDNA can be used for determining the primary structure of the protein and producing a large amount of the protein. Therefore, various cDNA cloning techniques have been developed which include isolating mRNA from cells, synthesizing cDNAs from the mRNA, and isolating a cDNA encoding a target protein.

The most important requisite for cDNA cloning is to synthesize a cDNA containing an entire protein coding region encoded by an intact mRNA. The intact mRNA contains a characteristic structure at the 5' terminal, so called a cap. The cDNA containing an entire sequence involving from the nucleotide at which the cap is added is called a "full-length cDNA". If a full-length cDNA is synthesized, one can know the whole information on the primary structure of a protein and also use it for mass production of the protein encoded by the cDNA. According to conventional terminology, a "full-length cDNA" has been used as a cDNA containing an entire coding region of the protein even if the cDNA contains no cap site sequence. In this invention, however, a "full-length cDNA" is defined only as a cDNA containing a nucleotide sequence starting from the cap site.

The Gubler-Hoffman method [Gene 25:263–269(1983)], which is most widely used for cDNA synthesis, could not give a full-length cDNA, because deletion at the terminals of cDNA occurs. On the other hand, the Okayama-Berg method [Mol.Cell.Biol. 2:161–170(1982)] is known to give a full-length cDNA at high efficiency. The characteristic feature of this method is to add a dC tail to the 3' end of the first strand cDNA synthesized from mRNA. This method, however, does not always give a full-length cDNA, because dC tailing also occurs on truncated cDNA generated by unexpected termination of cDNA synthesis. The truncated cDNAs originated from the degraded mRNAs are also synthesized.

DISCLOSURE OF THE INVENTION

It is therefore an object of the present invention to provide a method for selectively synthesizing a full-length cDNA containing a nucleotide sequence starting from a cap site of mRNA, and a cDNA containing whole information on the primary structure of a protein. Furthermore, another object of this invention is to provide a method to prepare an intermediate for synthesizing the full-length cDNA and to prepare a recombinant vector containing the full-length cDNA.

The inventors succeeded in synthesizing a full-length cDNA at high efficiency from mRNA whose cap structure was replaced by a DNA oligonucleotide or a DNA-RNA chimeric oligonucleotide.

The invention provides a process for producing an intermediate for the synthesis of a full-length cDNA, which comprises a step of treating mRNA extracted from cells with an alkaline phosphatase to eliminate the phosphate group from the 5' end of an uncapped degraded mRNA, a step of decapping from the 5' end of a capped intact mRNA, and a step of ligating either a DNA oligonucleotide or a DNA-RNA chimeric oligonucleotide represented by the following general formula [I] to the 5' end phosphate group formed in the above step by the action of T4 RNA ligase, thereby selectively adding either the DNA oligonucleotide or the DNA-RNA chimeric oligonucleotide having an arbitrary sequence to the 5' end of the intact mRNA.

$$5'\text{-dN}_1\text{-dN}_2\text{-}\ldots\text{-dN}_m\text{-N}_1\text{-N}_2\text{-}\ldots\text{-N}_n\text{-}3' \qquad [\text{I}]$$

wherein dN represents a deoxyribonucleotide selected from among dAMP, dCMP, dGMP and dTMP; N represents a ribonucleotide selected from among AMP, CMP, GMP and UMP; "-" represents a phosphoric ester linkage; m represents an integer of 1 or more, n represents an integer of 0 or more.

Furthermore, the invention provides a process for synthesizing a full-length cDNA, which comprises linking a double-stranded DNA primer having a dT tail by annealing to a poly(A) tail of the 3' end of the intact mRNA having the DNA oligonucleotide or the DNA-RNA chimeric nucleotide added at the 5' end as described above, and then synthesizing the first strand cDNA complementary to the intact mRNA by means of a reverse transcriptase.

Furthermore, the invention provides a process for preparing a recombinant vector containing a full-length cDNA, which comprises the steps involved in the process for synthesizing a full-length cDNA described above in which the sequence of the DNA oligonucleotide or the DNA-RNA oligonucleotide contains at least one site recognized by a restriction enzyme RE1 and the double-stranded DNA primer contains the same, the step of digesting with a restriction enzyme RE1 the material linked between the double-stranded DNA primer and the mRNA-cDNA hybrid prepared by the method described above, the step of circularizing the resultant material by self-libation, and the step of converting the RNA in the circularized recombinant vector to DNA.

The invention enables sure synthesis of a full-length cDNA which has been difficult to synthesize according to the conventional methods. Since a cDNA clone obtained from the cDNA library prepared according to the present method is sure to contain the whole information on the primary structure of the protein, the obtained clone can be used immediately to produce the encoded protein.

BEST MODE FOR CARRYING OUT THE INVENTION

Figure 1:
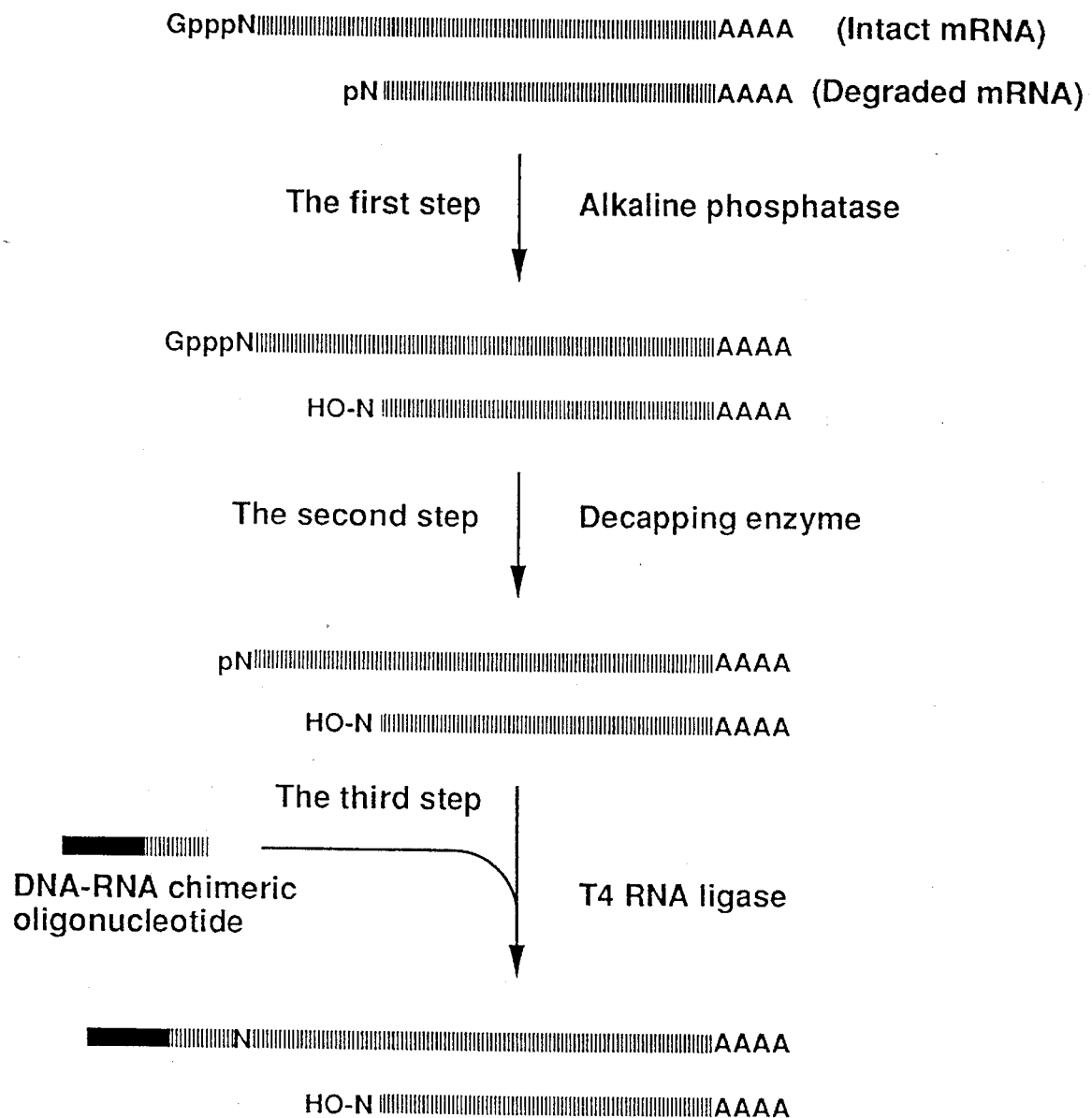
FIG. 1 shows a process for selectively ligating a DNA-RNA chimeric oligonucleotide to an intact mRNA possessing a cap.

This invention is directed to a method for synthesizing a full-length cDNA, including two processes. The first process consists of ligation of a DNA oligonucleotide or a DNA-RNA chimeric oligonucleotide to an intact mRNA possessing a cap and the second process consists of cDNA synthesis from the synthetic oligonucleotide-capped mRNA and production of a recombinant vector containing the cDNA. Each step in the first process is shown in FIG. 1. All steps in the first and second processes can be conducted using the conventional methods in this field.

The First Step

Usually mRNAs extracted from cells contain degraded mRNA possessing no cap structure. This step is carried out to remove the phosphate group of the degraded mRNA by means of an enzyme such as an alkaline phosphatase. Since an intact mRNA has a cap structure at the 5' end, the phosphatase does not affect the intact mRNA. The 5' end of a degraded mRNA possessing no cap structure is converted to a hydroxy group by selective dephosphorylation.

The Second Step

The cap structure of the intact mRNA is removed by a decapping enzyme to generate one phosphate group at the 5' end. The tobacco acid pyrophosphatase or T4 polynucleotide kinase can be exemplified as the decapping enzyme.

The Third Step

The DNA oligonucleotide or DNA-RNA chimeric oligonucleotide described by the following formula [I] is ligated to the 5'-terminal phosphate group of the decapped intact mRNA.

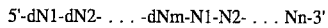

5'-dN1-dN2-....-dNm-N1-N2-... Nn-3'  [I]

wherein dN represents a deoxyribonucleotide selected from among dAMP, dCMP, dGMP and dTMP; N represents a ribonucleotide selected from among AMP, CMP, GMP and UMP; "-" represents a phosphoric ester linkage; m represents an integer of 1 or more; n represents an integer of 0 or above.

In order to facilitate the followed preparation of a recombinant vector containing the cDNA, the sequence of the deoxyribonucleotide preferably contains at least one site to be recognized by a restriction enzyme RE1. Any restriction enzyme RE1 which does not cut the DNA-RNA hybrid can be used, and one generating the protruding site is preferred. In this step the 5' end of the intact mRNA, which has a phosphate group generated at the second step mentioned above, can be incorporated with a DNA oligonucleotide or a DNA-RNA chimeric oligonucleotide. On the other hand, the 5' end of the degraded mRNA cannot be incorporated with it because of the hydroxyl group generated at the 5' end by dephosphorylation in the first step. Thus the DNA oligonucleotide or the DNA-RNA chimeric oligonucleotide is selectively added to the 5' end of the intact mRNA. Since T4 RNA ligase catalyzes the ligation between RNA strands more efficiently than between RNA and DNA strands, the use of a DNA-RNA chimeric oligonucleotide is preferred.

The DNA oligonucleotide or DNA-RNA chimeric oligonucleotide used in this process can be chemically synthesized in a tube or with an automatic DNA/RNA synthesizer. There have been no reports about a DNA-RNA chimeric oligonucleotide which is useful in the present invention in spite of the ease in which it can be synthesized, so that it is provided for the first time in accordance with the present invention.

It is preferable to use an excess molar ratio of the oligonucleotide to mRNA in the ligation reaction between the oligonucleotide and mRNA.

Figure 2:
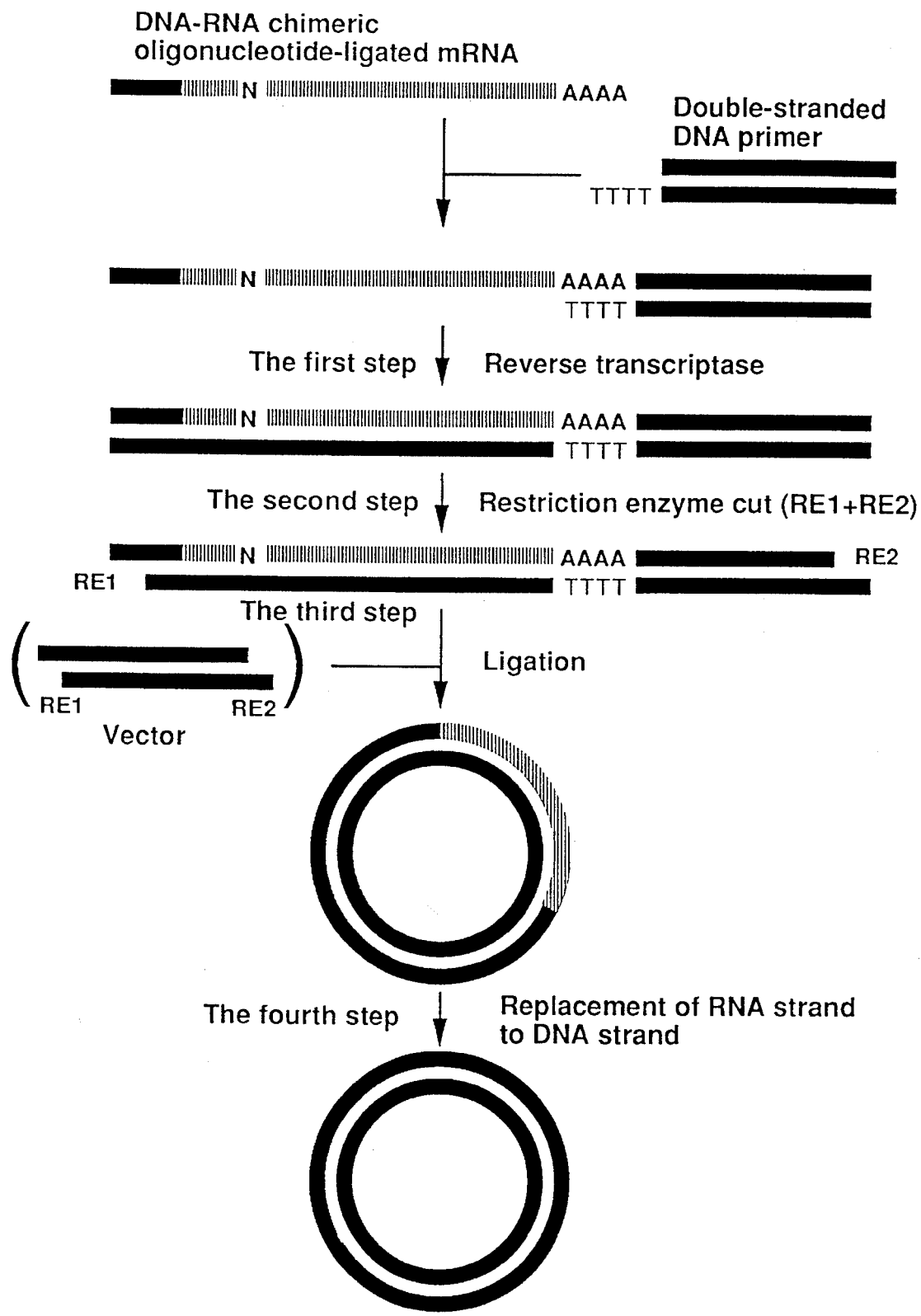
FIG. 2 shows a process for synthesizing cDNA from a synthetic oligonucleotide-ligated mRNA.

Each step of the second process is shown in FIG. 2.

The First Step

The mRNA capped by a DNA oligonucleotide or a DNA-RNA chimeric oligonucleotide, which was prepared in the first process, is annealed with a double-stranded DNA primer containing a tail of n (dT)s at the 3' end. Then, the first strand cDNA is synthesized using reverse transcriptase. The double-stranded DNA primer can be selected from an oligonucleotide, any double-stranded DNA fragment or any vector primer (for example, a plasmid DNA containing a replication origin of E. coli). The oligonucleotide primer can be chemically synthesized. In this case, n is preferably from 10 to 30. The latter two primers can be prepared by cutting the plasmid vector with a restriction enzyme generating a protruding 3' end and adding a dT-tail using terminal deoxynucleotidyl transferase. In this case, n is preferably from 50 to 70.

The double-stranded DNA primer preferably possesses at least one site for restriction enzyme RE2 near the end to which the dT-tail is not added for easy preparation of a recombinant vector containing a cDNA. Any restriction enzyme RE2, preferably one generating a protruding end by digestion, can be used as long as it does not cut a mRNA-cDNA hybrid. The RE1 and RE2 should be identical when a vector primer is used, although they could be different when an oligonucleotide primer or a DNA fragment primer is used.

The synthesis of the first strand cDNA complementary to an intact mRNA is completed by the first step described above. The following second, third, and fourth steps are those for preparing a recombinant vector containing the synthesized cDNA.

The Second Step

When two restriction sites for RE1 and RE2 are used, the synthesized product containing the first strand cDNA is digested with both RE1 and RE2 to generate the corresponding restriction end at both ends of the double-stranded DNA parts. When no restriction sites exist in these parts, any restriction end can be prepared by adding linkers to the ends with T4 DNA ligase and digesting them with the corresponding restriction enzymes according to the conventional method. The blunt ends can be used without digestion with restriction enzymes.

The Third Step

This is a step for inserting the obtained cDNA into an appropriate cloning vector for E. coli. The procedure depends on the used primer. When an oligonucleotide primer or a DNA fragment primer is used, the cDNA fragment prepared in the second step is ligated to any cloning vector (including plasmid, cosmid, phage, etc.) for E. coli after digesting it with restriction enzymes RE1 and RE2. If a linker is used for preparing the restriction ends in the second step, the vector should be digested with the restriction enzymes corresponding to the site designed in the linker, or the corresponding linker should be added to the ends of the vector prior to ligation to the cDNA fragment. In either case, the ligation between blunt ends can be carried out without digestion with restriction enzymes.

The Fourth Step

The RNA strand in the vector is replaced by a DNA strand using RNase H, *E. coli* DNA polymerase I, and *E. coli* DNA ligase according to the conventional method.

The above procedure allows preparation of a recombinant vector containing a cDNA complementary to an intact mRNA.

The recombinant vector prepared by the above procedure can be used to transform host cells such as *E. coli*. The plasmid, cosmid, and phage, etc. prepared from the transformants contain the full-length cDNA. Thus, these processes give a clone containing a full-length cDNA.

The present invention will now be described by way of examples, but various changes and modifications can be made without departing from the invention.

REFERENCE EXAMPLES (1) Preparation of mRNA

A model mRNA was prepared from the cDNA encoding human ribosomal phosphoprotein P1 (described in Japanese Laid-open Patent Application (Kokai) No. 4-117292). Five µg of the cDNA plasmid was digested with NotI and then used as a template for in vitro transcription using a kit purchased from Boehringer Mannheim. By adding m7G(5')ppp(5')G in the reaction mixture, the cap was added to the 5' end of the transcribed RNA. When the product was analyzed by formamide-containing agarose gel electrophoresis, a single band of c.a. 600 nucleotides was shown on the gel. This was used as a model mRNA for cDNA synthesis. This model mRNA is composed of the vector-derived sequence starting from the cap, the sequence derived from the mRNA encoding human ribosomal phosphoprotein P1, and about 100 nucleotides of poly(A) tail. Not all mRNAs synthesized above contain the cap at the 5' end.

(2) Synthesis of DNA-RNA Chimeric Oligonucleotide

The oligonucleotide described by the following formula (SEQ. I.D. NO.: 1) was synthesized with a DNA synthesizer (Applied Biosystems, model 392) using the phosphoramidite method.

5'-dG-dG-dG-dG-dA-dA-dT-dT-dC-dG-dA-G-G-A-3'

Reagents for RNA synthesis and DNA synthesis were purchased from Peninsula and ABI, respectively. First, the adenine-CPG column was set on the synthesizer. Then, two ribonucleotides (G) followed by the other deoxyribonucleotides were added in order of above sequence under the reaction conditions described in the protocol. Finally, the synthesized oligomer was cut in an ammonia-ethanol (3:1) solution. The protected groups were removed by treating with THF at 55° C. for 10 h. The product was purified on polyacrylamide gel electrophoresis.

(3) Synthesis of DNA Oligonucleotide

The DNA oligonucleotide described by the following formula (SEQ. I.D. NO.: 2), was synthesized with a DNA synthesizer (Applied Biosystems, model 392) using the phosphoramidite method.

5'-dG-dG-dG-dG-dA-dA-dT-dT-dC-dG-dA-dG-dG-dA-3'

The reaction conditions described in the protocol were used. The product was purified on polyacrylamide gel electrophoresis according to the conventional method.

(4) Preparation of the DNA Fragment Primer

One hundred µg of the pKA1 vector primer possessing a tail of c.a. 60 (dT)s (described in Japanese Laid-open Patent Application (Kokai) No. 4-117292) was digested with 100 units of the restriction enzyme NdeI. The 500 bp fragment containing a (dT) tail was isolated on 1.5% agarose gel electrophoresis. The resultant fragment was used as a DNA fragment primer.

EXAMPLE 1

One hundred µg of the model mRNA encoding human ribosomal phosphoprotein P1, which was prepared in the above REFERENTIAL EXAMPLE, was dissolved in 100 mM Tris-HCl (pH 8.0). After adding one unit of RNase-free bacterial alkaline phosphatase (Takara Shuzo), the reaction mixture was incubated at 37° C. for one hour. After phenol extract and ethanol precipitation of the reaction mixture, the pellet was dissolved in a solution containing 50 mM sodium acetate (pH 6.0), 1 mM EDTA, 0.1% mercaptoethanol, and 0.01% Triton X-100. After adding one unit of tobacco acid phosphatase (Epicentre Technologies), the reaction mixture of total 100 µl was incubated at 37° C. for one hour. After phenol extract and ethanol precipitation of the reaction mixture, the pellet was dissolved in distilled water.

Fifteen pmoles of the decapped mRNA and 150 pmoles of the DNA-RNA chimeric oligonucleotide synthesized in the above REFERENTIAL EXAMPLE were dissolved in a 100 µl solution containing 75 mM Tris-HCl (pH 7.5), 0.1 mM ATP, 10 mM $MgCl_2$, 5 mM dithiothreitol, and 10 µl of DMSO. After adding 100 units of T4 RNA ligase (Takara Shuzo), the reaction mixture was incubated at 16° C. for 16 hours. After phenol extract and ethanol precipitation of the reaction mixture, the pellet was dissolved in distilled water.

Three µg of the DNA-RNA chimeric oligonucleotide-ligated mRNA and 1.5 µg of a pKA1 vector primer possessing a tail of c.a. 60 (dT)s (described in Japanese Laid-open Patent Application (Kokai) No. 4-117292) were dissolved in a solution containing 50 mM Tris-HCl (pH 8.3), 75 mM KCl, 3 mM $MgCl_2$, 10 mM dithiothreitol, 1.25 mM dNTPs-(dATP+dCTP+dGTP+dTTP). After adding 200 units of reverse transcriptase (Takara Shuzo), the reaction mixture of total 20 µwas incubated at 42° C. for one hour. After phenol extract and ethanol precipitation of the reaction mixture, the pellet was dissolved in a solution containing 20 mM Tris-HCl (pH 7.5), 100 mM KCl, 4 mM $MgCl_2$, 10 mM $(NH_4)_2SO_4$, and 50 µg/ml bovine serum albumin. Then the reaction mixture was added by 60 units of *E. coli* DNA ligase (Takara Shuzo) and incubated at 16° C. for 16 hours. After adding 2 µl of 2 mM dNTPs, 4 units of *E. coli* DNA polymerase (Takara Shuzo) and 0.1 unit of *E. coli* RNase H (Takara Shuzo) the reaction mixture was incubated at 12° C. for one hour and then at 22° C. for one hour.

Mixing 10 μl of the reaction mixture with 100 μl of *E. coli* HB101 competent cells, the transformation of HB101 was carried out according to the conventional method. The transformants grew on an ampicillin-containing LB agar plate. Twelve colonies generated on the plate were picked up, suspended in 3 ml of an ampicillin-containing LB medium, and incubated overnight. The plasmids were isolated from the cultured cells by the alkaline lysis method. The isolated plasmids were digested with EcoRI and NotI and analyzed on agarose gel electrophoresis. Each plasmid contained a cDNA insert of c.a. 600 bp. The sequence of the cDNA terminal was determined by the dideoxy method. The results showed that each cDNA possessed the sequence starting from the cap site of the model mRNA downstream of the synthetic oligonucleotide-derived sequence including an EcoRI site.

EXAMPLE 2

Five μg of rabbit globin mRNA (BRL) was dephosphorylated and decapped by the same way as described in EXAMPLE 1. Thirty pmoles of the obtained mRNA and 3 nmoles of the DNA-RNA chimeric oligonucleotide synthesized in the REFERENTIAL EXAMPLE were dissolved in a solution containing 50 mM Tris-HCl (pH 7.5), 0.5 mM ATP, 5 mM $MgCl_2$, 10 mM 2-mercaptoethanol, and 25% polyethylene glycol. After adding 50 units of T4 RNA ligase (Takara Shuzo), the reaction mixture of total 30 μl was incubated at 20° C. for 12 hours. After phenol extract and ethanol precipitation of the reaction mixture, the pellet was dissolved in distilled water.

After the reaction product was annealed with a pKA1 vector primer, cDNA synthesis and transformation of *E. coli* by the resultant cDNA vector were carried out under the same conditions as described in EXAMPLE 1. Twelve colonies were randomly picked up from the agar plate. After incubation in the medium, the plasmid was isolated from the cultured cells. Since a rabbit globin cDNA has one EcoRI site at position c.a. 400 from the cap site, the full-length cDNA encoding rabbit globin should produce the fragment of 400 bp by EcoRI digestion. In fact, the double digestion of every plasmid with EcoRI and NotI produced two bands including c.a. 400 bp and c.a. 250 bp originated from the cDNA and one band corresponding to the vector. These results suggested that every plasmid contained the full-length cDNA for globin. In order to confirm this, the 5' terminal sequences were determined. The results showed that each cDNA possessed the sequence starting from the cap site of the rabbit globin mRNA downstream of the synthetic oligonucleotide-derived sequence including an EcoRI site. The starting material, rabbit globin mRNA, was composed of alpha-globin mRNA and beta-globin mRNA. Out of 12 clones analyzed, 4 clones contained the full-length cDNA encoding alpha-globin and the remaining 8 clones contained that encoding beta-globin.

EXAMPLE 3

Using a DNA oligonucleotide prepared in REFERENCE EXAMPLE 3 instead of a DNA-RNA chimeric oligonucleotide, cDNA synthesis was carried out in the same manner as described in the above EXAMPLE. The number of transformants decreased by one tenth, but the sequence analysis of 5' end of cDNA isolated from the transformants showed that every clone contained the full-length cDNA encoding rabbit alpha- or beta-globin.

EXAMPLE 4

Three μg of the DNA-RNA chimeric oligonucleotide-ligated rabbit globin mRNA prepared in EXAMPLE 2 was annealed with 1.5 μg of the DNA fragment primer prepared in the REFERENCE EXAMPLE, and then cDNA synthesis was carried out under the same conditions as described in EXAMPLE 1. The product was digested with 50 units of EcoRI and 50 units of NotI, and ligated to 1 μg of EcoRI, NotI-digested pKA1 (described in Japanese Laid-open Patent Application (Kokai) No. 4-117292). The reaction mixture was used for transformation of *E. coli*. The plasmid was prepared from each transformant. The double digestion of every plasmid with EcoRI and NotI produced two bands including c.a. 400 bp and c.a. 250 bp on agarose gel electrophoresis. The 5' terminal sequences were determined by the dideoxy method. The results showed that each clone possessed the full-length cDNAs encoding the rabbit alpha- or beta-globin downstream of the synthetic oligonucleotide-derived sequence including an EcoRI site.

EXAMPLE 5

Ten μg of poly(A)$^+$RNA prepared from human fibrosarcoma cell line HT-1080 using the conventional method was dephosphorylated and then decapped in the same way as described in EXAMPLE 1. The obtained poly(A)$^+$RNA and 3 nmoles of the DNA-RNA chimeric oligonucleotide synthesized in REFERENCE EXAMPLE were dissolved in a solution containing 50 mM Tris-HCl (pH 7.5), 0.5 mM ATP, 5 mM $MgCl_2$, 10 mM 2-mercaptoethanol, and 25% polyethylene glycol. After adding 50 units of T4 RNA ligase (Takara Shuzo), the reaction mixture of total 30 μl was incubated at 20° C. for 12 hours. After phenol extract and ethanol precipitation of the reaction mixture, the pellet was dissolved in distilled water.

After the reaction product was annealed with the pKA1 vector primer, cDNA synthesis and transformation of *E. coli* by the resultant cDNA vector were carried out under the same conditions as described in EXAMPLE 1. Six hundred colonies were randomly picked up from the agar plate. After incubation in the medium, the plasmids were isolated from the cultured cells. Determining the 5' terminal sequence of each cDNA clone, it was discovered many cDNAs encoded proteins identical to known human proteins. In some genes encoding these proteins, their transcription initiation sites on the genomic sequence have already been determined, and thus was compared to the 5' terminal sequence of the obtained cDNA. In the case of abundant housekeeping proteins such as elongation factor 1-alpha, various ribosomal proteins and so on, the 5' terminal sequence of the cDNA agreed with the sequence of the transcription initiation site. These results mean that the cDNA is full-length. Nine out of 10 clones encoding elongation factor 1-alpha contained the full-length cDNA (starting from 5'-CTTTTTCGCAA . . . (SEQ. I.D. NO.: 3)).

INDUSTRIAL AVAILABILITY

The invention enables sure synthesis of a full-length cDNA. Since a cDNA clone obtained from the cDNA library prepared according to the present method is sure to contain the whole information on the primary structure of the protein, the obtained clone can be used immediately to produce the encoded protein. Therefore, the present invention is useful for production of useful proteins by genetic engineering.

We claim:

1. A process for producing an intermediate for the synthesis of a full-length cDNA, which process comprises the steps of:

treating mRNA extracted from cells with an alkaline phosphatase to eliminate the phosphate group from the 5' end of an uncapped degraded mRNA;

decapping the 5' end of a capped intact mRNA; and ligating by the action of T4 RNA ligase either a DNA oligonucleotide or a DNA-RNA chimeric oligonucleotide to the 5' end phosphate group formed in the above decapping step, thereby selectively adding either the DNA oligonucleotide or the DNA-RNA chimeric oligonucleotide to the 5' end of the intact mRNA, wherein the DNA oligonucleotide or the DNA-RNA chimeric oligonucleotide has the following formula (I)

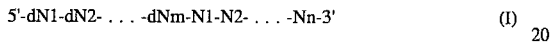
                                                 (I)

and wherein dN represents a deoxyribonucleotide selected from dAMP, dCMP, dGMP and dTMP; N represents a ribonucleotide selected from AMP, CMP, GMP and LIMP; "-" represents a phosphoric ester linkage; m represents an integer of 1 or more; and n represents an integer of 0 or more.

2. The process according to claim 1, wherein said DNA oligonucleotide or said DNA-RNA chimeric oligonucleotide represented by the formula (I) contains at least one recognition site of a restriction enzyme RE1 which does not cleave a DNA/RNA hybrid duplex.

3. A process for synthesizing a full-length cDNA, which process comprises: annealing a double-stranded DNA primer having a dT tail to a poly(A) tail of the 3' end of the intact mRNA having the DNA oligonucleotide or the DNA-RNA chimeric oligonucleotide added at the 5' end produced by the process according to claim 1, and then synthesizing the first strand cDNA complementary to the intact mRNA by a reverse transcriptase.

4. A process for synthesizing a full-length cDNA, which process comprises: annealing a double-stranded DNA primer having a dT tail to a poly (A) tail of the 3' end of the intact mRNA having the DNA oligonucleotide or the DNA-RNA chimeric oligonucleotide added at the 5' end produced by the process according to claim 2, and then synthesizing the first strand cDNA complementary to the intact mRNA by a reverse transcriptase.

5. A process for preparing a recombinant vector containing a full-length cDNA, which process comprises the steps of:

synthesizing a full-length cDNA by the process of claim 4 wherein the double-stranded DNA primer is a vector primer containing at least one recognition site of the restriction enzyme RE1;

digesting the product of the synthesizing step with said restriction enzyme;

circularizing the resultant digested material by self-ligation; and converting the RNA in the circularized recombinant vector to DNA.

6. A process for preparing a recombinant vector containing a full-length cDNA, which process comprises the steps of:

synthesizing a full-length cDNA by the process of claim 4, wherein the double-stranded DNA primer is a vector primer containing at least one recognition site of restriction enzyme RE2;

digesting the product of the synthesizing step with said restriction enzymes RE1 and RE2 at said recognition sites for said restriction enzymes to produce a digested material having a recognition site for restriction enzyme RE1 at one end and a recognition site for restriction enzyme RE2 at the other end thereof;

recombining the resultant digested material with a vector having a recognition site for restriction enzyme RE1 at one end and a recognition site for restriction enzyme RE2 at the other end thereof to prepare a circularized recombinant vector; and converting the RNA in the circularized recombinant vector to DNA.

7. A DNA-RNA chimeric oligonucleotide of the formula (I):

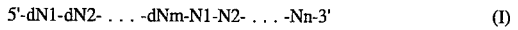
                                                 (I)

wherein dN represents a deoxyribonucleotide selected from dAMP, dCMP, dGMP and dTMP; N represents a ribonucleotide selected from AMP, CMP, GMP and UMP; "-" represents a phosphoric ester linkage; m represents an integer of 1 or more; and n represents an integer of 1 or more, wherein said DNA-RNA chimeric oligonucleotide contains at least one recognition site of a restriction enzyme in the DNA moiety of said chimeric oligonucleotide.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Chimeric DNA-RNA
            oligonucleotide"

( i i i ) HYPOTHETICAL: YES ( i v ) ANTI-SENSE: NO ( i x ) FEATURE:
        ( A ) NAME/KEY: misc_feature
        ( B ) LOCATION: 12..14
        ( D ) OTHER INFORMATION: /note= "GGA at positions 12-14 are
            ribonucleotides"

( x i ) SEQUENCE DESCRIPTION: SEQ ID NO:1:

GGGGAATTCG AGGA        14

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA
            oligonucleotide"

( i i i ) HYPOTHETICAL: YES ( i v ) ANTI-SENSE: YES ( x i ) SEQUENCE DESCRIPTION: SEQ ID NO:2:

GGGGAATTCG AGGA        14

( 2 ) INFORMATION FOR SEQ ID NO:3:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "5'end of full-length cDNA
            of human elongation factor 1-alpha"

( i i i ) HYPOTHETICAL: NO ( i v ) ANTI-SENSE: NO ( x i ) SEQUENCE DESCRIPTION: SEQ ID NO:3:

CTTTTTCGCA A        11